(12) United States Patent
Otani et al.

(10) Patent No.: US 7,697,745 B2
(45) Date of Patent: Apr. 13, 2010

(54) ENCLOSURE INSPECTION METHOD AND APPARATUS THEREOF

(75) Inventors: Chiko Otani, Wako (JP); Yoshiaki Sasaki, Wako (JP); Gosei Okazaki, Matsuyama (JP); Kazunori Ninomiya, Matsuyama (JP); Masahiro Yamashita, Matsuyama (JP); Kengo Takahashi, Matsuyama (JP); Atsushi Takasuka, Matsuyama (JP); Toru Kitaguchi, Matsuyama (JP)

(73) Assignees: Riken, Wako-shi, Saitama (JP); S.I Seiko Co., Ltd., Ehime (JP)

( * ) Notice: Subject to any disclaimer, the term of this patent is extended or adjusted under 35 U.S.C. 154(b) by 823 days.

(21) Appl. No.: 11/452,525

(22) Filed: Jun. 14, 2006

(65) Prior Publication Data

US 2007/0009085 A1 Jan. 11, 2007

(30) Foreign Application Priority Data

Jun. 27, 2005 (JP) ............................. 2005-187143

(51) Int. Cl.
*G06K 9/00* (2006.01)
*G01N 23/04* (2006.01)
*G01J 5/00* (2006.01)

(52) U.S. Cl. ...................... 382/132; 378/57; 250/338.1
(58) Field of Classification Search ................... 382/132
See application file for complete search history.

(56) References Cited

U.S. PATENT DOCUMENTS 5,202,692 A * 4/1993 Huguenin et al. ........... 342/179
5,227,800 A * 7/1993 Huguenin et al. ........... 342/179
5,642,393 A * 6/1997 Krug et al. ..................... 378/57
2006/0022140 A1* 2/2006 Connelly et al. ......... 250/338.1

FOREIGN PATENT DOCUMENTS

JP 10-090174 4/1998
JP 2001-066375 3/2001
JP 3387721 1/2003

\* cited by examiner

*Primary Examiner*—Samir A. Ahmed
*Assistant Examiner*—Fred Hu
(74) *Attorney, Agent, or Firm*—Flynn, Thiel, Boutell & Tanis, P.C.

(57) ABSTRACT

In an enclosure inspection apparatus 11, when a sealed letter 2 is inputted into a sealed letter loading station A, visual inspecting means 27 and X-ray inspecting means 33 determine thickness of the sealed letter and whether an enclosure in the sealed letter is a predetermined suspected object. The sealed letter not less than a predetermined thickness is rejected in first sorting station D, and the sealed letter which is not thicker than the predetermined thickness and in which the suspected object is not detected is conveyed as it is to second sorting station G. As for the sealed letter which is not thicker than the predetermined thickness and in which the suspected object is detected, after the suspected object in the sealed letter is positioned in a positioning station E, a suspected object inspecting station F determines whether the above-described suspected object is a predetermined object, such as an explosive or a narcotic drug, using a terahertz wave.

It is possible to detect promptly the presence of the objects even if there are a large number of sealed letters.

8 Claims, 5 Drawing Sheets

ENCLOSURE INSPECTION METHOD AND APPARATUS THEREOF

FIELD OF THE INVENTION

The present invention relates to an enclosure inspection method and apparatus thereof, and in particular, relates to an enclosure inspection method of inspecting an enclosure in an inspection object and apparatus thereof.

DESCRIPTION OF THE PRIOR ART

Nowadays, in order to prevent propagation of terrorism and drugs, there has been an increasing need for inspecting an enclosure in an inspection object such as a sealed letter to check whether or not the enclosure is such an object as an explosive, a drug, and the like.

In addition to the sealed letter, a postcard with a concealing seal, a parcel, and the like may be considered as the inspection objects. In order to inspect an enclosure in such inspection objects without opening them, it has been proposed to irradiate the inspection object with an electromagnetic wave such as a terahertz wave or a millimeter wave to check whether or not the enclosure is the object.

Inspecting means using a terahertz wave or a millimeter wave has been disclosed in Japanese Patent No. 3387721, Japanese Patent Laid-Open No. 10-90174, and Japanese Patent Laid-Open No. 2001-66375. When the object is irradiated with the terahertz wave or millimeter wave, scattered, transmitted, and reflected waves of the terahertz wave or millimeter wave vary with the type of the object. Therefore, it is possible to determine whether the enclosure is the object by detecting the scattered, transmitted, and reflected waves.

However, there has been a problem of difficulties to handle a large number of inspection objects in a short time because it needs much time to determine an object in the inspection objects using the terahertz wave or millimeter wave.

SUMMARY OF THE INVENTION

In consideration of such a problem, the present invention provides an enclosure inspection method and its apparatus capable of promptly determining, even with a large number of inspection objects, whether or not the enclosure is the object.

An enclosure inspection method of claim 1 is characterized by radiating X-rays from the exterior of an inspection object to image the inspection object; determining whether a suspected object is enclosed as an enclosure in the inspection object from the obtained X-ray image; radiating a terahertz wave or a millimeter wave to the suspected object from the exterior of the inspection object in which the suspected object is enclosed; and determining whether the suspected object is a predetermined object by detecting a scattered wave, a transmitted wave, or a reflected wave of the terahertz wave or millimeter wave.

An enclosure inspection apparatus of claim 4 is characterized by comprising X-ray inspecting means of radiating X-rays from the exterior of an inspection object to image the inspection object and determining whether the suspected object is enclosed as an enclosure in the inspection object from the obtained X-ray image; and suspected object inspecting means of radiating a terahertz wave or a millimeter wave to the inspection object which is determined to have the suspected object enclosed therein from the exterior of the inspection object, and determining whether the suspected object is a predetermined object by detecting a scattered wave, a transmitted wave, or a reflected wave of the terahertz wave or millimeter wave.

DETAILED DESCRIPTION OF THE EMBODIMENTS

Figure 1:
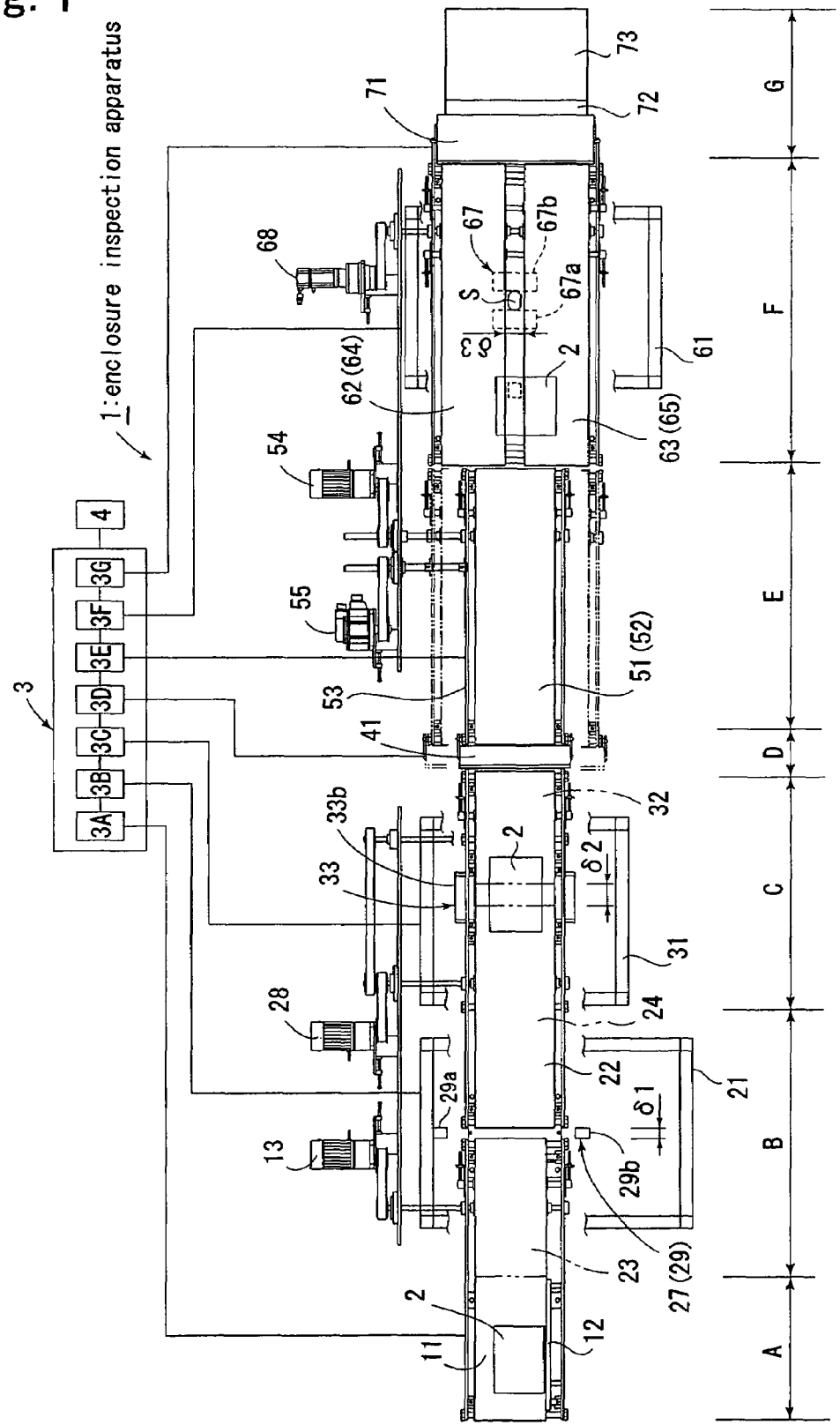
FIG. 1 shows a plan view of an enclosure inspection apparatus according to the present invention.

Exemplary embodiments will be described below. FIG. 1 shows a plan view of an enclosure inspection apparatus 1 according to the present invention, which is an apparatus which detects a predetermined object enclosed in a sealed letter 2 as an inspection object. Here, FIG. 1 is drawn with a portion above a conveyance face of the sealed letter 2 being omitted.

The enclosure inspection apparatus 1 of this embodiment is constructed of a sealed letter loading station A into which the sealed letter 2 is inputted, a visual inspecting station B which performs an visual inspection of the sealed letter 2, an X-ray inspecting station C which determines whether an enclosure in the sealed letter 2 is a predetermined suspected object, a first sorting station D which rejects the sealed letter 2 depending on the enclosure, a positioning station E which positions the suspected object in the sealed letter 2, a suspected object inspecting station F which determines whether the suspected object is a predetermined object, and a second sorting station G which sorts out the sealed letter 2 depending on the enclosure.

Then, this entire enclosure inspection apparatus 1 is controlled by control means 3. This control means 3 is equipped with, for each station, a sealed letter loading station controller 3A, a visual inspecting station controller 3B, an X-ray inspecting station controller 3C, a first sorting station controller 3D, a positioning station controller 3E, a suspected object inspecting station controller 3F, and a second sorting station controller 3G. In addition, a data storage 4 which stores inspection data every sealed letter 2 in each inspecting station is connected thereto.

The object in this embodiment means an enclosure such as a hazardous substance like an explosive, or a banned drug like a narcotic drug, and the suspected object means an enclosure, which is suspected as the object, among enclosures enclosed in the sealed letter 2. Because such objects have not been detectable visually from appearance of the sealed letter 2, it has been difficult to detect the objects in the sealed letter 2.

First, operation of the enclosure inspection apparatus 1 of this embodiment will be briefly explained. When the sealed letter 2 is inputted into the sealed letter loading station A, thickness and appearance of the sealed letter 2 is checked in the visual inspecting station B, and then it is determined whether the enclosure in the sealed letter 2 is the suspected object and a position of a suspected object within the sealed letter 2 is detected in the X-ray inspecting station C.

The first sorting station D rejects the sealed letter 2 not less than a predetermined thickness, and the positioning station E moves the sealed letter 2, which is determined to have the suspected object enclosed therein in the X-ray inspecting station C, so that the suspected object in the sealed letter 2 may arrive at a predetermined radiating position S in the suspected object inspecting station F.

In the suspected object inspecting station F, it is determined whether the suspected object in the sealed letter 2 is a predetermined object using a terahertz wave, and in the second sorting station G, one sealed letter 2 in which the object is enclosed is sorted from another sealed letter 2 in which it is not enclosed, according to the determination.

Figure 2:
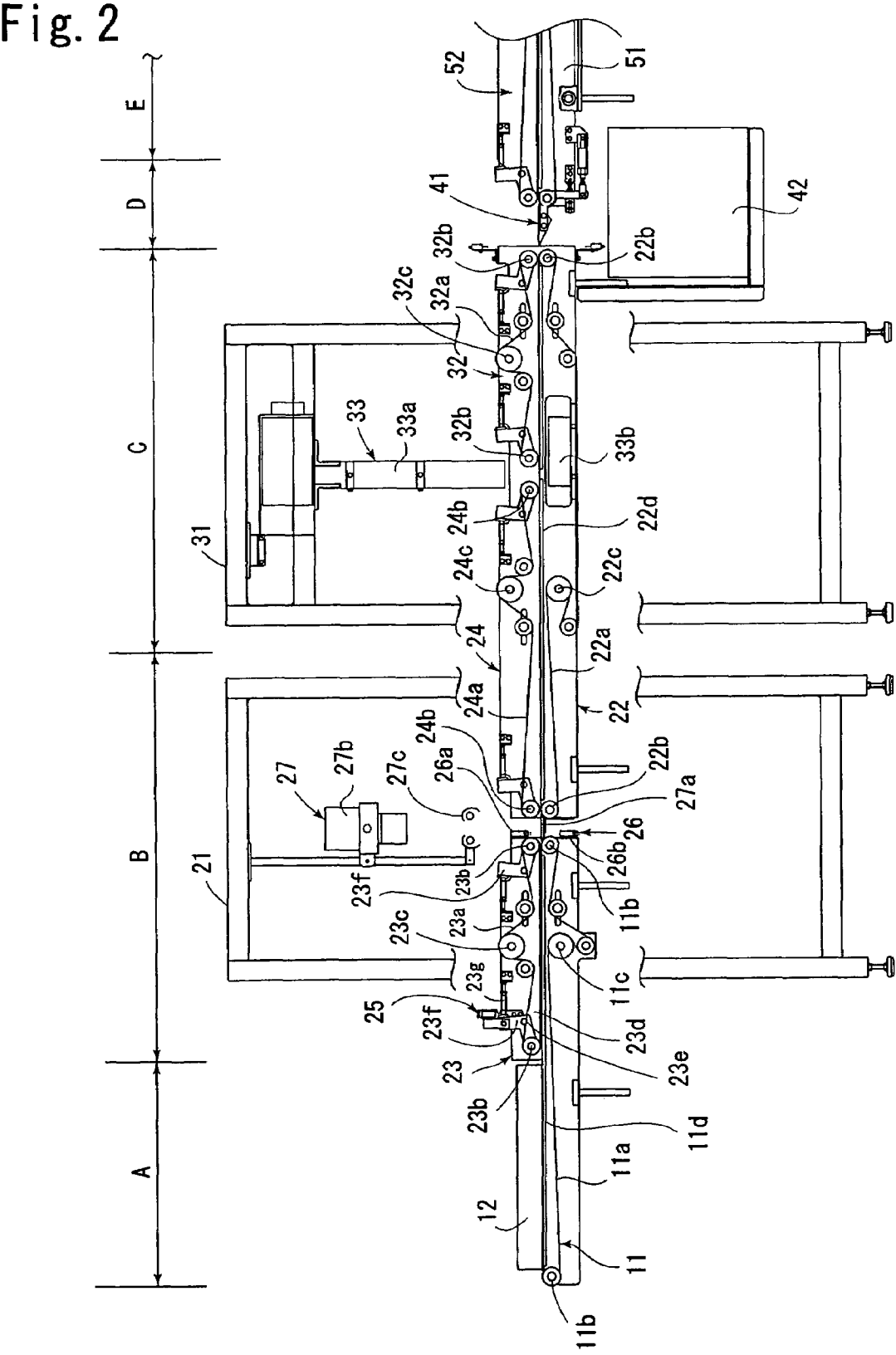
FIG. 2 shows a side view of an upstream of the enclosure inspection apparatus.

Each station will be explained below. As shown in FIGS. 1 and 2, the sealed letter loading station A is equipped with a first carrying conveyor 11 on a top face of which the sealed letter 2 is conveyed, and a guide bar 12 provided in one side of the first carrying conveyor 11. The sealed letter supply means not shown supplies the sealed letter 2 to the top face of the first carrying conveyor 11.

The first carrying conveyor 11 is equipped with a holding roller 11b which provides an endless belt 11a in a tensioned state, and a drive roller 11c which rotates the belt 11a. Among these, the holding roller 11b in a downstream end is located in a case 21 of the visual inspecting station B, and the drive roller 11c is rotated by a first motor 13 installed outside the case 21.

In addition, between both the holding rollers 11b, a guide plate 11d which guides the travel of the belt 11a so that the top face of the belt 11a cannot be loosened.

The guide bar 12 is provided along one side of the first carrying conveyor 11, and the sealed letter 2 is supplied on the belt 11a relative to the guide bar 12 with one side of the sealed letter 2 being substantially contacted with the guide bar 12.

The visual inspecting station B is equipped with a case 21, a second carrying conveyor 22 which receives the sealed letter 2 from the first carrying conveyor 11, first and second pressure conveyors 23 and 24 which sandwiches the sealed letter 2 between these first and second carrying conveyors 11 and 22 to prevent a positional offset of the sealed letter 2, thickness detecting means 25 of detecting the thickness of the sealed letter 2, sealed letter detecting means 26 of detecting front end and rear end positions of the sealed letter 2 which is conveyed, and visual inspecting means 27 of inspecting the appearance of the sealed letter 2.

The case 21 is provided in order to prevent invasion of disturbance light at the time of an inspection by the visual inspecting means 27, and an opening portion which is not shown is formed in a portion in which the first and second carrying conveyors 11 and 22, and first and second pressure conveyors 23 and 24 are installed.

The second carrying conveyor 22 is equipped with an endless belt 22a made of a radiolucent material, two holding rollers 22b which provide the endless belt 22a in a tensioned state, and a drive roller 22c which rotates the belt 22a, and the drive roller 22c is rotated by a second motor 28 installed out of the case 21.

In addition, between both the holding rollers 22b, a guide plate 22d, which guides the travel of the belt 22a so that the top face of the belt 22a cannot be loosened, is provided except an X-ray radiating position (gap $\delta 2$) by the following X-ray inspecting means 33.

Then, between the holding roller 22b in an upstream of the second carrying conveyor 22, and the holding roller 11b in a downstream of the first carrying conveyor 11, a gap $\delta 1$ is formed as a visual inspecting position by the visual inspecting means 27. In addition, the holding roller 22b in the downstream of the second carrying conveyor 22 is located in an end portion of the X-ray inspecting station C.

The first pressure conveyor 23 is equipped with swing rollers 23b which provide an endless elastic belt 23a in a tensioned state, and a drive roller 23c which rotates the elastic belt 23a. The swing roller 23b in the upstream is provided in the middle of the first carrying conveyor 11, and the swing roller 23b in the downstream is provided in the same position as the holding roller 11b in the downstream of the first carrying conveyor 11, respectively.

The drive roller 23c is driven by the first motor 13, and the first pressure conveyor 23 is driven at the same conveying speed as the first carrying conveyor 11.

Each swing roller 23b is rotatably supported in a tip portion of a swing arm 23f swingably supported by a rotation axis 23e in both sides of a frame 23d, and each spring 23g is installed elastically between another tip portion of each swing arm 23f, and the frame 23d.

Then, with the elasticity of the spring 23g, and the tension of the elastic belt 23a, each swing arm 23f is energized in one direction, and usually, each swing roller 23b contacts the top face of the belt 11a of the first carrying conveyor 11.

For this reason, the sealed letter 2 supplied to the sealed letter loading station A is conveyed by the first carrying conveyor 11 to reach the first pressure conveyor 23, and advances between the belts 11a and 23a of both the conveyors 11 and 23 while pushing up the swing roller 23b against the elasticity of the spring 23g and the tension of the elastic belt 23a. Thereby, the positional offset of the sealed letter 2 is prevented.

Detailed explanation will not be repeated because the second pressure conveyor 24 has the similar structure as the first pressure conveyor 23. Nevertheless, the second pressure conveyor 24 is equipped with swing rollers 24b which provide an endless elastic belt 24a in a tensioned state, and a drive roller 24c which rotates the elastic belt 24a. The swing roller 24b in an upstream is provided in the same position as the holding roller 22b in the upstream of the second carrying conveyor 22, and the swing roller 24b in a downstream is provided in a case 31 of the X-ray inspecting station C, respectively.

The drive roller 24c is driven by the second motor 28, and hence, the second pressure conveyor 23 is driven in the same conveying speed as the second carrying conveyor 22.

Figure 3:
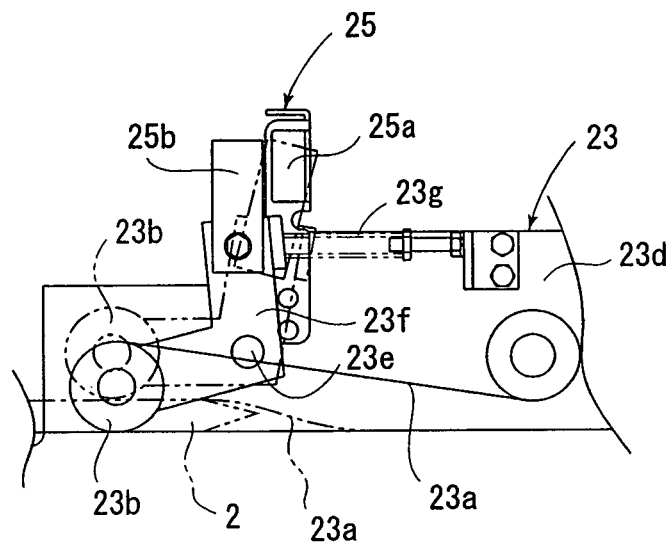
FIG. 3 shows an enlarged side view about thickness detecting means.

As shown in FIG. 3, the thickness detecting means 25 is constructed of a sensor 25a fixed in the upstream of the frame 23d in the first pressure conveyor 23, and a plate 25b fixed to a top of the swing arm 23f in an upstream in the first pressure conveyor 23.

When the sealed letter 2 advances between the first carrying conveyor 11 and the first pressure conveyor 23, the swing roller 23b is pushed up and the plate 25b moves. When the sensor 25a detects that the amount of movement is larger than a predetermined amount, a signal for rejecting the sealed letter 2 is sent to the first sorting station controller 3D.

Alternatively, a rotation shaft 23e of the first pressure conveyor 23 may be integrally connected with the swing arm 23f, and the sensor 25a may be a sensor which detects an amount of the movement of the swing roller 23b from a rotation angle of the rotation shaft 23e.

The sealed letter detecting means 26 is provided in the downstream end of the first carrying conveyor 11 and the first pressure conveyor 23, and is constructed of a light emitting element 26a and a photodetector 26b which are provided in upper and lower sides of a conveying path of the sealed letter 2.

When the front end of the sealed letter 2 projects from between the first carrying conveyor 11 and the first pressure conveyors 23, light from the light emitting element 26a which is incident into the photodetector 26b is interrupted, and the tip position of the sealed letter 2 is detected. When the sealed letter 2 finishes passing, the photodetector 26b will receive the light from the light emitting element 26a again, and the rear end position of the sealed letter 2 will be detected.

Then, when the sealed letter detecting means 26 detects the tip position of the sealed letter 2, the visual inspecting station controller 3B activates the visual inspecting means 27 to start a visual inspection of the sealed letter 2. When the sealed letter detecting means 26 detects the rear end position of the sealed letter 2, the visual inspecting station controller 3B calculates the time of a rear end position of the sealed letter 2 passing a gap δ1 on the basis of the conveying speed of the second carrying conveyor 22 to activate the visual inspecting means 27 until the sealed letter 2 finishes passing through the gap δ1.

As shown in FIGS. 1 and 2, the visual inspecting means 27 is constructed of a support plate 27a provided in a position of the gap δ1, a line camera 27b fixed above the gap δ1, an illumination light 27c irradiating the gap δ1, and an area sensor 29 fixed through a bracket, which is not shown, to a side of the gap δ1. This visual inspecting means 27 makes it possible to obtain appearance of the sealed letter 2, such as color and size, as an image.

The support plate 27a is fixed with being aligned in a position of a conveyance face of the first and second carrying conveyors 11 and 22, and becomes a guide at the time of delivering the sealed letter 2 to the second carrying conveyor 22 from the first carrying conveyor 11.

The line camera 27b images a top face linearly when the sealed letter 2 passes the gap δ1 to image the whole top face of the sealed letter 2. The illumination light 27c is provided along an image-sensing range of the camera 27b.

Alternatively, it is also possible to cause the line camera 27b to image light transmitted through the sealed letter 2, by providing a transparent support plate 27a, and the illumination light 27c located in a lower face side of the support plate 27a.

Furthermore, the area sensor 29 is constructed of a pair of light emitting element 29a and a photodetector 29b, as shown in FIG. 1, which are provided in accordance with conveyance height of the sealed letter 2 respectively, and are also provided so as to sandwich the sealed letter 2 on the second carrying conveyor 22.

Then, it is made to measure the thickness of the sealed letter 2 continuously without touching the sealed letter 2 by the photodetector 29b detecting a portion where light from the light emitting element 29a is screened by the sealed letter 2 when the sealed letter 2 passes the gap δ1.

The X-ray inspecting station C is equipped with a case 31, a third pressure conveyor 32 which is arranged in a downstream of the second pressure conveyor 24, and prevents the positional offset of the sealed letter 2 which is conveyed between with the second carrying conveyors 22, and X-ray inspecting means 33 of determining the presence of a suspected object in the sealed letter 2.

The case 31 prevents X-rays, radiated by the X-ray inspecting means 33, from diffusing outside, and an opening portion which is not shown is formed in a portion in which the second carrying conveyor 22, and second and third pressure conveyors 24 and 32 are installed.

Detailed explanation will not be repeated because the third pressure conveyor 32 has the similar structure as the first and second pressure conveyors 23 and 24. Nevertheless, the third pressure conveyor 32 is equipped with swing rollers 32b which provide an endless elastic belt 32a in a tensioned state, and a drive roller 32c which rotates the elastic belt 32a.

The swing roller 32b in an upstream of this third pressure conveyor 32 is provided in a position apart by a gap δ2 from the swing roller 24b in a downstream of the second pressure conveyer 24. The swing roller 32b in the downstream is provided in the same position as the holding roller 22b in the downstream of the second carrying conveyor 22.

Then, the drive roller 32c is driven by the second motor 28, and the third pressure conveyor 32 is driven at the same conveying speed as the second carrying conveyor 22. In addition, an X-ray inspecting position by the X-ray inspecting means 33 is provided in the gap δ2.

The X-ray inspecting means 33 is equipped with an X-ray radiating portion 33a which is installed above the gap δ2, and radiates X-rays toward the sealed letter 2, and a line-type X-ray camera 33b which receives X-rays which are transmitted through the sealed letter 2 and the belt 22a of the second carrying conveyor 22. These X-ray radiating portion 33a and X-ray camera 33b are installed in the case 31 through brackets, respectively.

The X-ray inspecting station controller 3C calculates a time at which the sealed letter 2 arrives at the gap δ2 and a time at which it finishes passing on the basis of a detected signal of front end and rear end positions of the sealed letter 2 in the sealed letter detecting means 26 of the visual inspecting station B and the conveying speed of the second carrying conveyor 22, and causes the X-ray camera 33b to image the sealed letter 2 while the sealed letter 2 passes through the gap δ2 so as to obtain an X-ray image.

Furthermore, the X-ray inspecting station controller 3C determines the presence of a suspected object in the sealed letter 2 by the X-ray image which the X-ray camera 33b images. When the suspected object is detected, the X-ray inspecting station controller 3C detects a coordinate value of the suspected object in the sealed letter 2 and transmits the coordinate value of this suspected object to the positioning station controller 3E.

The first sorting station D is equipped with first sorting means 41 which sorts out a predetermined sealed letter 2, and a first reject box 42 in which the sorted sealed letter 2 is contained, and the first sorting means 41 is controlled by the first sorting station controller 3D provided in the control means 3.

Figure 4:
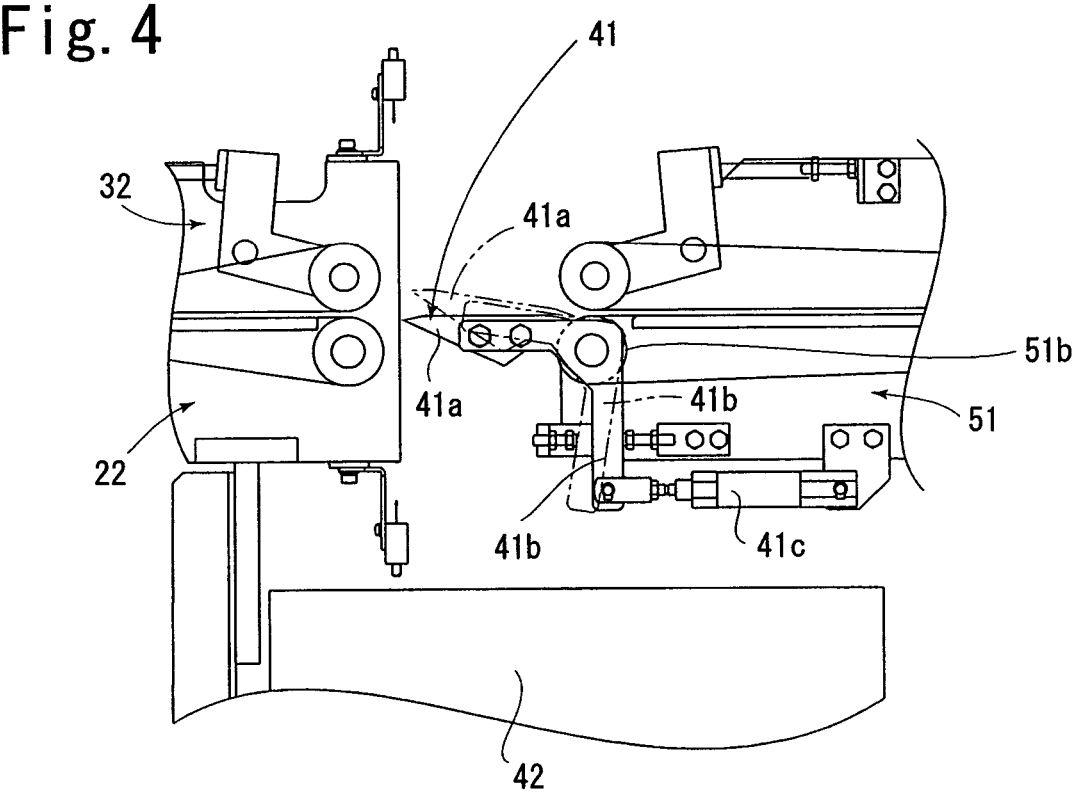
FIG. 4 shows an enlarged side view about first sorting means.

As shown in FIG. 4, the first sorting means 41 is provided in the upper end of the third carrying conveyor 51 which constitutes the positioning station E, and is equipped with a flap 41a provided between the second carrying conveyor 22 and the third carrying conveyor 51, a swing arm 41b which rotates the flap 41a on the same axis as the holding roller 51b in the upstream of the third carrying conveyor 51, and an air cylinder 41c which energizes the swing arm 41b, and opens and closes the flap 41a up and down.

The flap 41a is usually located so that its top face may become flush with conveyance faces of the second and third carrying conveyors 22 and 51, and when a lower portion of the swing arm 41b is energized to the left on the drawing by the air cylinder 41c, the front end of the flap 41a opens upper than the conveyance face of the second carrying conveyor 22.

Then, as explained in detail later, the first sorting station D rejects the sealed letter 2 not less than a predetermined thickness into the first reject box 42. Then, when this sealed letter 2 is conveyed on the second carrying conveyor 22, the front end of the flap 41a is opened, and the sealed letter 2 advances into the lower face side of the flap 41a, and is rejected into the first reject box 42.

Figure 5:
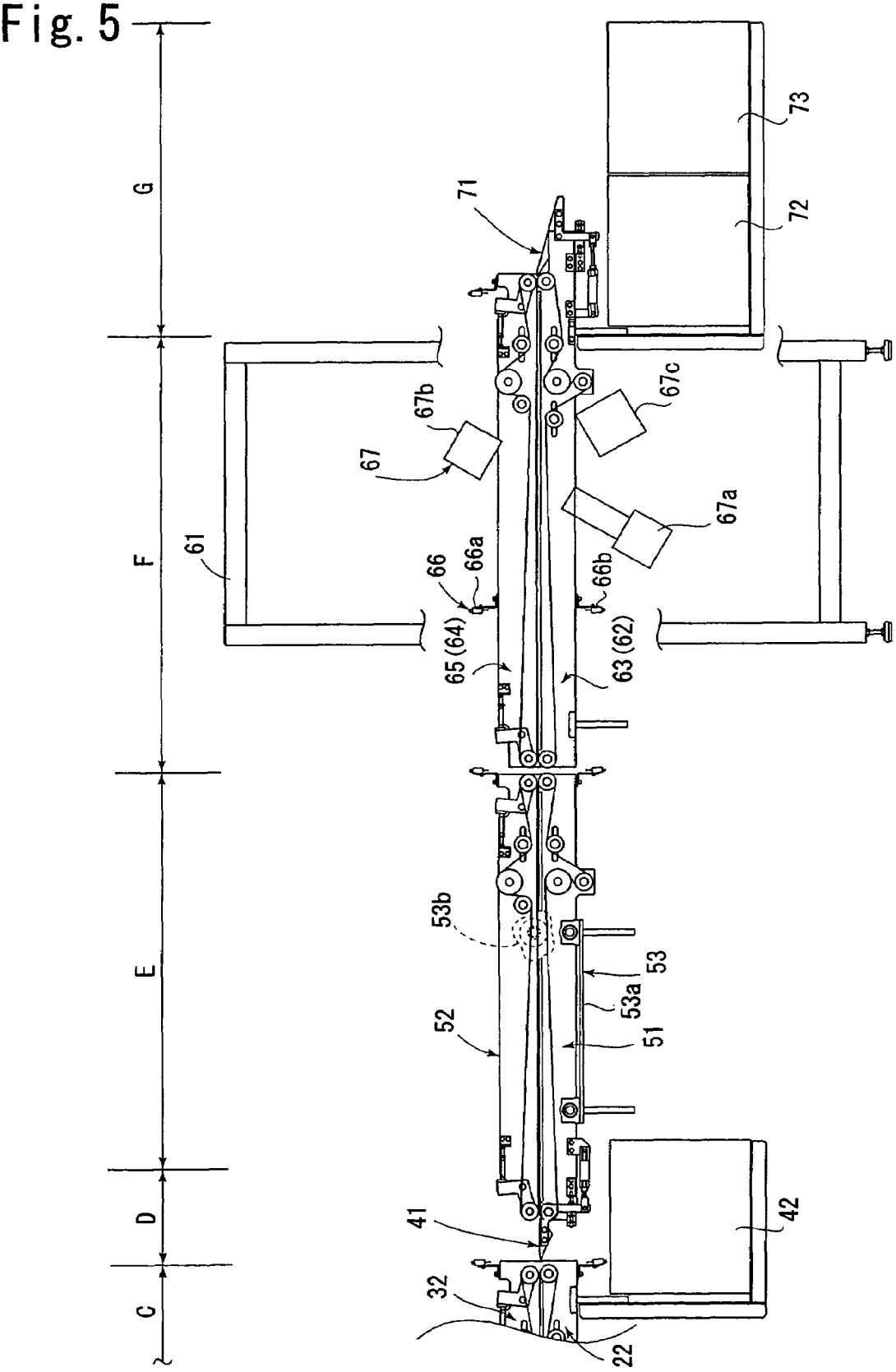
FIG. 5 shows a side view of a downstream of the enclosure inspection apparatus.

As shown in FIGS. 1 and 5, the positioning station E is equipped with a third carrying conveyor 51 which conveys the sealed letter 2, a fourth pressure conveyor 52 which prevents a positional offset of the sealed letter 2 conveyed on the third carrying conveyor 51, and positioning means 53 of moving these third carrying conveyor 51 and fourth pressure conveyor 52 in a direction orthogonal to a transfer direction of the sealed letter 2.

Detailed explanation will not be repeated because the third carrying conveyor 51 and fourth pressure conveyor 52 have the similar structure as the first and second carrying conveyors 11 and 22, and the first to third pressure conveyors 23, 24 and 32. Nevertheless, these are driven respectively at the same conveying speed by a third motor 54 provided adjacently to the positioning station E.

The positioning means 53 is equipped with a movable frame 53a holding the third carrying conveyor 51 and fourth pressure conveyor 52, and a ball screw 53b provided in a direction orthogonal to the transfer direction from a side face of the movable frame 53a.

The ball screw 53b is driven by a first servo-motor 55 provided adjacently to the positioning station E, and it is possible to move the movable frame 53a in a direction orthogonal to the transfer direction in a state that the third carrying conveyor 51 and fourth pressure conveyor 52 are driven.

Then, the positioning station controller 3E activates the positioning means 53 in the case of the sealed letter 2, in which the suspected object is enclosed, among the sealed letters 2 which are not rejected in the first sorting station D, and moves the sealed letter 2 to a position where a center of the suspected object in the sealed letter 2 arrives at a predetermined radiating position S of the suspected object inspecting station F.

On the other hand, in the case of the sealed letter 2 in which the suspected object is not enclosed, the positioning station controller 3E does not activate the positioning means 53, and makes the sealed letter 2 conveyed as it is.

The suspected object inspecting station F is equipped with a holding frame 61, fourth and fifth carrying conveyors 62 and 63 which receive the sealed letter 2 from the positioning station E and are arranged in parallel, fifth and sixth pressure conveyors 64 and 65 which are provided above these fourth and fifth carrying conveyors 62 and 63 respectively, sealed letter detecting means 66 of detecting the sealed letter 2 conveyed on the fourth and fifth carrying conveyor 62 and 63, and a suspected object inspecting means 67 of inspecting whether a suspected object in the sealed letter 2 is a predetermined object.

The fourth and fifth carrying conveyors 62 and 63 have the similar structure as the first to third carrying conveyors 11, 22, and 51 respectively. The fourth carrying conveyor 62 and fifth carrying conveyor 63 are arranged in a gap δ3 in parallel, and these are driven respectively at the same conveying speed by a second servomotor 68 provided outside the holding frame 61.

A radiating position S by the suspected object inspecting means 67 is set in a predetermined position of the gap δ3 as an inspecting position, and a terahertz wave is radiated on the sealed letter 2 which passes through the radiating position S.

In addition, the fifth and sixth pressure conveyors 64 and 65 have the similar structure as the first to fourth pressure conveyors 23, 24, 32, and 52 respectively. These are spaced apart by the gap δ3 in parallel, and are driven by the second serve-motor 68 at the same conveying speed as the fourth and fifth carrying conveyors 62 and 63 respectively.

For this reason, the sealed letter 2 is held from beneath by the fourth and fifth carrying conveyors 62 and 63, and is conveyed in a state of being sandwiched by the fifth and sixth pressure conveyors 64 and 65 from above so as not to deviate.

Although the second servomotor 68 is used to convey the sealed letter 2 by changing the conveying speed of the sealed letter 2, a usual motor may be used to convey the sealed letter 2 at a fixed conveying speed.

The sealed letter detecting means 66 is provided in an upper stream than the radiating position S, and is constructed of a light emitting element 66a and a photodetector 66b, which are provided in upper and lower sides of the conveying path of the sealed letter 2, in a position of the gap δ3.

When the front end of the sealed letter 2 arrives between the light emitting element 66a and photodetector 66b, light incident into the photodetector 66b from the light emitting element 66a is interrupted, and the tip position of the sealed letter 2 is detected. When the sealed letter 2 finishes passing, the photodetector 66b receives the light from the light emitting element 66a, and the rear end position of the sealed letter 2 is detected.

Then, when the sealed letter detecting means 66 detects the tip position of the sealed letter 2, the suspected object inspecting station controller 3F activates the suspected object inspecting means 67 in response to the suspected object in the sealed letter 2 arriving at the radiating position S, on the basis of the detected result in the X-ray inspecting station C and the speeds of the fourth and fifth carrying conveyors 62 and 63.

The suspected object inspecting means 67 is equipped with a terahertz wave irradiator 67a which irradiates a terahertz wave, a first detector 67b provided in a position of sandwiching the sealed letter 2 with the terahertz wave irradiator 67a, and a second detector 67c provided in an installation side of the terahertz wave irradiator 67a side by side, and these are fixed to the holding frame 61 through a bracket which is not shown.

The terahertz wave irradiator 67a irradiates a terahertz wave whose frequency becomes from 100 THz to 0.1 THz respectively in the radiating position S, when a wavelength is from 3 μm to 3 mm. The first detector 67b detects a transmitted wave of the terahertz wave, which is transmitted through the suspected object, or a scattered wave scattered at the time of the terahertz wave being transmitted through the suspected object. The second detector 67c detects a reflected wave of a terahertz wave, which is reflected by the suspected object, or a scattered wave scattered when the terahertz wave is reflected by the suspected object.

Here, the transmitted wave is an electromagnetic wave which is detected by the first detector 67b as it is after a radiated terahertz wave is transmitted through a suspected object. The reflected wave is an electromagnetic wave which is detected by the second detector 67c as it is after a radiated terahertz wave is reflected by a suspected object. The scattered wave is an electromagnetic wave other than a transmitted wave or a reflected wave which is dispersed when the terahertz wave is transmitted through or reflected by a suspected object, and is detected by the first detector 67b or the second detector 67c.

Then, the suspected object inspecting station controller 3F determines whether the suspected object is a predetermined object from strength of a transmitted wave, a reflected wave, and a scattered wave which the first and second detectors 67b and 67c detect, etc., and according to a determined result, a signal for activating the second sorting station G is transmitted to the second sorting station controller 3G.

Of course, the wavelength and frequency of the terahertz wave are not limited to the ranges, and they may be more or less deviated.

The second sorting station G is equipped with second sorting means 71 which sorts out the sealed letter 2 depending on the presence of an object, a second reject box 72 which withdraws the sealed letters 2 in which the object is detected, and a third reject box 73 which withdraws the sealed letters 2 in which then object is not detected, and the second sorting means 71 is controlled by the second sorting station controller 3G.

Figure 6:
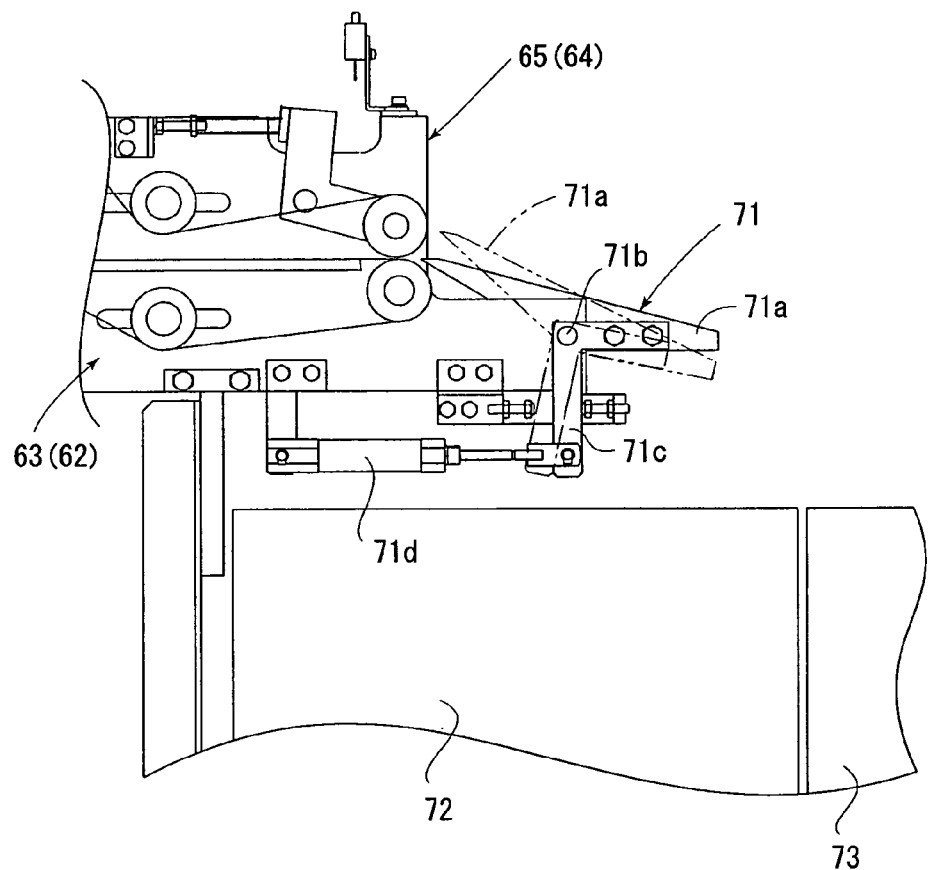
FIG. 6 shows an enlarged side view about second sorting means.

As shown in FIG. 6, the second sorting means 71 is equipped with a flap 71a provided in the downstream end of the fourth and fifth carrying conveyors 62 and 63 which construct the suspected object inspecting station F, a swing arm 71c which rotates the flap 71a with centering a rotation shaft 71b, and an air cylinder 71d which energizes the swing arm 71c to open and close the flap 71a up and down.

The flap 71a is usually located so that its top face may become flush with conveyance faces of the fourth and fifth carrying conveyors 62 and 63, and when a lower portion of the swing arm 71c is energized to the left on the drawing by the air cylinder 71d, the front end of the flap 71a opens upper than the conveyance faces of the fourth and fifth carrying conveyors 62 and 63.

Then, the second sorting station G rejects the sealed letter 2, in which the object is detected, into the second reject box 72, and rejects the sealed letter 2, in which the object is not detected is rejected into the third reject box 73.

Hence, when this sealed letter 2 in which the object is sealed is conveyed on the fourth and fifth carrying conveyors 62 and 63, the front end of the flap 71a is opened, and the sealed letter 2 advances into the lower face side of the flap 71a, and is rejected into the second reject box 72.

Hereafter, operation of the enclosure inspection apparatus 1 which has the structure will be explained.

First, when the enclosure inspection apparatus 1 is activated, each conveyor starts operation at a predetermined conveying speed by the control means 3, and the sealed letter 2 is supplied on the first carrying conveyor 11 of the sealed letter loading station A by the sealed letter supply means, which is not shown, from this state.

Then, one side of the supplied sealed letter 2 is positioned relative to the guide bar 12, and the sealed letter 2 is conveyed by the first carrying conveyor 11 to the visual inspecting station B.

The first pressure conveyor 23 of the visual inspecting station B is driven by the first motor 13 at the same conveying speed as the first carrying conveyor 11. When the sealed letter 2 on the first carrying conveyor 11 comes to the first pressure conveyor 23, the swing roller 23b in an upstream is pushed up by the sealed letter 2, and the sealed letter 2 is conveyed in a state of being sandwiched by the first carrying conveyor 11 and first pressure conveyor 23.

At this time, because the swing arm 23f which rotatably support a shaft of the swing roller 23b by the swing roller 23b being pushed up by the sealed letter 2, the plate 25b of the thickness detecting means 25 provided in another end of the swing arm 23f moves.

Movement more than a predetermined amount of the plate 25b is detected by the sensor 25a fixed to the frame 23d, and a signal showing the state is transmitted to the first sorting station controller 3D.

Next, when a tip portion of the sealed letter 2 projects from between the first carrying conveyor 11 and first pressure conveyors 23, the light from the light emitting element 26a of the sealed letter detecting means 26 to the photodetector 26b is screened by the sealed letter 2, the tip position of the sealed letter 2 is detected. Then, the rear end position of the sealed letter 2 is detected because the photodetector 26b receives light again.

On the other hand, in the visual inspecting station B, the second carrying conveyor 22 and second pressure conveyor 24 are driven at the same conveying speed as the first carrying conveyor 11, and the sealed letter 2 is supplied between the second carrying conveyor 22 and second pressure conveyor 24 through the gap δ1.

While this sealed letter 2 passes through the gap δ1, the visual inspecting station controller 3B activates the visual inspecting means 27 on the basis of the signal from the photodetector 26b, irradiates the sealed letter 2 from the illumination light 27c, and images the sealed letter 2 by the line camera 27c.

The image imaged by the line camera 27b is transmitted to the data storage 4, and information about appearance, such as color and size of the sealed letter 2, which the line camera 27b images is stored every sealed letter 2.

On the other hand, the area sensor 29 measures the thickness of the sealed letter 2 and the data storage 4 also stores this as information about the appearance of the sealed letter 2.

Alternatively, the area sensor 29 may be used as thickness detecting means and the sensor 25a and the like may be omitted. In this case, sorting may be performed in the first sorting station D on the basis of the thickness of the sealed letter 2 measured by using the area sensor 29.

Next, when the sealed letter 2 is conveyed to the X-ray inspecting station C, the X-ray inspecting station controller 3C calculates time when the sealed letter 2 arrives at the gap 62 as an X-ray inspecting position from the information on the tip and rear end position of the sealed letter 2 which the visual inspecting station controller 3B recognized by the sealed letter detecting means 26, and performs an inspection by the X-ray inspecting means 33 from just before the sealed letter 2 arriving at the gap δ2 to finishing passing.

The X-ray inspecting means 33 radiates X-rays from the X-ray radiating portion 33a, X-rays which are transmitted through the sealed letter 2 are imaged by the X-ray camera 33b, and an X-ray image is transmitted to the X-ray inspecting station controller 3C.

The X-ray inspecting station controller 3C determines whether the enclosure in the sealed letter 2 is a suspected object from the X-ray image of the sealed letter 2 imaged.

Figure 7:
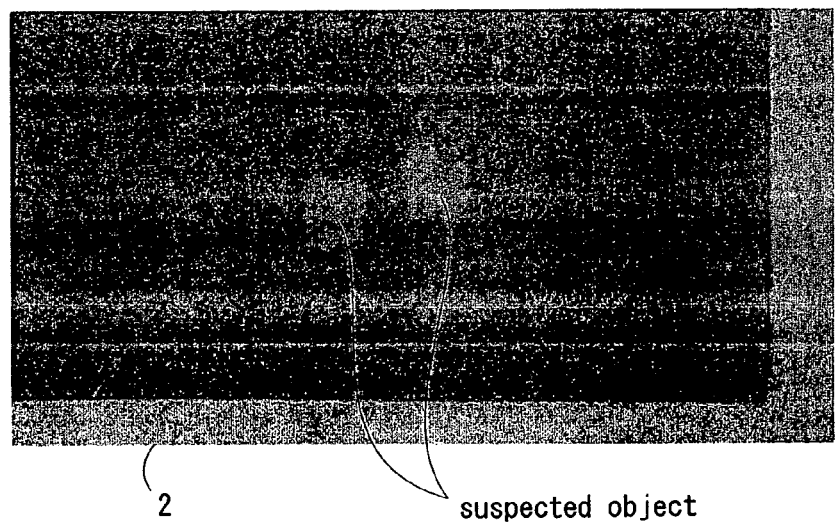
FIG. 7 shows an example of an X-ray image by X-ray inspecting means.

FIG. 7 shows an example of the X-ray image which the X-ray camera 33b images, and the suspected object is enclosed inside the sealed letter 2 as an enclosure.

Here, the suspected object also includes other substances, which do not fall under the object, in addition to the objects such as hazardous substances like an explosive, and banned drugs like a narcotic drug. Although these suspected objects have a common feature in that they do not transmit X-rays thoroughly, it is not possible to determine only by an inspection by X-rays whether an enclosure is the object.

For this reason, when the X-ray camera 33b images an enclosure which does not transmit X-rays thoroughly, the X-ray inspecting station controller 3C of this embodiment determines that this enclosure is a suspected object as it is suspected to be the object.

Alternatively, the X-ray inspecting station controller 3C may be used to perform image recognition such that an article which does not fall under the object apparently from its shape (such as a clip attached to a document) is not treated as a suspected object even if it is an enclosure imaged by the X-ray camera 33b.

Then, when a suspected object is detected in the sealed letter 2, the X-ray inspecting station controller 3C not only calculates a coordinate value of the suspected object in the sealed letter 2, but also transmits the coordinate value to the object positioning station controller 3E.

When passing through the gap δ2, the sealed letter 2 is continuously conveyed by the second carrying conveyor 22 and third pressure conveyor 32, and this sealed letter is sorted according to the following criteria in the first sorting station D.

When the sealed letter 2 not less than a predetermined thickness comes to the first sorting station D, the first sorting station controller 3D activates the air cylinder 41c of the first sorting means 41 according to the signal received from the visual inspecting station controller 3B, and raises a tip of the flap 41a.

Then, the sealed letter 2 with the condition is contained in the first reject box 42 provided below, and thereafter, it is inspected by other method whether the enclosure in the sealed letter 2 is the object.

In this way, a reason why the sealed letter 2 not less than the predetermined thickness is rejected is because there may arise a case that it is not possible to determine accurately the presence of the object in the suspected object inspecting means 67 because it is not possible to perform an inspection in a short time when the object is not less than the predetermined thickness.

Then, when the sealed letter 2 which is not rejected, that is, the sealed letter 2 thinner than the predetermined thickness comes to the first sorting station D, the first sorting station controller 3D does not activate the first sorting means 41. Hence, the sealed letter 2 is conveyed to the positioning station E which is a next step, as it is.

Next, in the positioning station E, the movable frame 53a of the positioning means 53 is positioned beforehand so that a position of the third carrying conveyor 51 coincides with a position of the second carrying conveyor 22 of the X-ray inspecting station C.

Then, in the positioning station E, the third carrying conveyor 51 and fourth pressure conveyor 52 are driven at the same conveying speed as the second carrying conveyor 22, and the sealed letter 2 is transferred from the second carrying conveyor 22 and third pressure conveyor 32 to the third carrying conveyor 51 and fourth pressure conveyor 52.

When the sealed letter 2 is thoroughly delivered to the third carrying conveyor 51 and fourth pressure conveyor 52, the positioning station controller 3E activates the positioning means 53 according to a position of the enclosure in the sealed letter 2 as follows.

First, in the case of the sealed letter 2 which is determined not to enclose the suspected object, the positioning station controller 3E does not activate the positioning means 53, and makes the sealed letter 2 conveyed to the suspected object inspecting station F as it is.

On the other hand, in the case of the sealed letter 2 which is determined to have the suspected object enclosed therein, the positioning station controller 3E activates the first servo-motor 55, rotates the ball screw 53b of the positioning means 53, and moves the movable frame 53a in a direction orthogonal to the conveying direction of the sealed letter 2.

At this time, the positioning station controller 3E moves the movable frame 53a so that the center of the suspected object may arrive at the radiating position S in the suspected object inspecting station F from the coordinate value of the suspected object in the sealed letter 2 which is received from the X-ray inspecting station controller 3C.

In the suspected object inspecting station F, the fourth, and fifth carrying conveyors 62 and 63, and the fifth and sixth pressure conveyors 64 and 65 are made to be driven by the second servo-motor 68 at the same conveying speed as the third carrying conveyor 51 and fourth pressure conveyor 52. The sealed letter 2 is received by these conveyors.

In the case of the sealed letter 2 in which the suspected object is enclosed, the suspected object inspecting station controller 3F controls the second servomotor 68 to decelerate the conveying speed. Furthermore, when the sealed letter detecting means 66 detects the sealed letter 2, the suspected object inspecting station controller 3F causes the suspected object inspecting means 67 to perform an inspection in response to the suspected object arriving at the radiating position S on the basis of the conveying speed and the coordinate value of the suspected object in the sealed letter 2 which is sent from the X-ray inspecting station controller 3C.

When the terahertz wave irradiator 67a radiates a terahertz wave on the suspected object which arrives at the radiating position S, a part of the terahertz wave is transmitted through the suspected object, and the first detector 67b detects the transmitted wave which is transmitted through this suspected object, or a scattered wave scattered at the time of being transmitted.

On the other hand, a part of the terahertz wave is reflected on the suspected object, and the second detector 67c detects a reflected wave which is reflected by this suspected object, or a scattered wave scattered at the time of being reflected.

The suspected object inspecting station controller 3F determines whether the suspected object is the above-described object from strength of the transmitted wave, reflected wave, and scattered wave which the first and second detectors 67b and 67c detect, etc., and transmits a signal relating to a determined result to the second sorting station controller 3G.

The suspected object inspecting means 67 has such publicly-known structure conventionally that is disclosed in the Japanese Patent No. 3387721, Japanese Patent Laid-Open No. 10-90174, and Japanese Patent Laid-Open No. 2001-66375. In addition, because a method of determining whether a suspected object is an object has also been known conventionally, detailed explanation is omitted.

On the other hand, about the sealed letter 2 whose enclosure is not a suspected object, the suspected object inspecting station controller 3F makes the sealed letter 2 conveyed to the second sorting station G without decelerating the conveying speed, and activating the suspected object inspecting means 67.

Finally, in the second sorting station G, the second sorting station controller 3G controls the second sorting means 71 according to the signal with regard to the determined result from the suspected object inspecting station controller 3F as follows.

First, when the object is enclosed in the sealed letter 2, the air cylinder 71c is controlled for the flap 71a to be opened, and the sealed letter 2 passes a lower face side of the flap 71a to be contained into the second reject box 72.

On the other hand, when the object is not enclosed in the sealed letter 2, the air cylinder 71d is controlled for the flap 71a to be closed, and the sealed letter 2 passes an upper face side of the flap 71a to be contained into the third reject box 73.

As mentioned above, the enclosure inspection apparatus 1 of this embodiment does not perform an inspection by a terahertz wave for the sealed letter 2 not less than the predetermined thickness, and the sealed letter 2 (sealed letter in which a suspected object is not detected) in which the object cannot be enclosed, but performs an inspection, using a terahertz wave, only for the sealed letter 2 (sealed letter in which the suspected object is detected) to be determined with the terahertz wave.

In this way, using the enclosure inspection apparatus 1 according to this embodiment, it is possible to promptly determine whether enclosures are the objects even if there are a large number of sealed letters 2.

Alternatively, in the embodiment, the first sorting station D may be omitted, and first to third reject boxes may instead be provided in the second sorting station G.

Then, three kinds of sealed letters may be contained in the first to third reject boxes by also using the second sorting means 71 of the second sorting station G as the first sorting means 41, and changing an angle of the flap 71a into three steps.

Also in this case, positioning in the positioning station E and an inspection in the suspected object inspecting station F may be omitted on the sealed letter 2 in which a suspected object is not detected, and the sealed letter 2 not less than the predetermined thickness.

In addition, a third sorting means may be provided between the positioning station E and suspected object inspecting station F, and the sealed letter 2 in which a suspected object is not enclosed may be rejected in the X-ray inspecting station C.

Furthermore, the terahertz wave irradiator 67a is used for the suspected object inspecting means 67 in this embodiment. Nevertheless, it is possible to perform a similar inspection also using a millimeter wave irradiator which radiates a millimeter wave whose frequency becomes 330 GHz to 33 GHz respectively when a wavelength is 1 mm to 10 mm.

In this case, the first detector 67b of the suspected object inspecting means 67 detects a transmitted wave of the millimeter wave, which is transmitted through the suspected object, or a scattered wave scattered at the time of the millimeter wave being transmitted through the suspected object. The second detector 67c detects a reflected wave of the millimeter wave, which is reflected by the suspected object, or a scattered wave scattered when the millimeter wave is reflected by the suspected object.

Of course, the wavelength and frequency of the millimeter wave are not limited to the ranges, and they may be more or less deviated.

What is claimed is:

1. An enclosure inspection sorting method, comprising:
   providing an enclosure inspection device having an X-ray inspecting device, a thickness detector, and an inspection device;
   using the thickness detector to determine whether or not an inspection object is thicker than a predetermined thickness while conveying the inspection object;
   radiating X-rays, using an X-ray radiator, onto the inspection object to determine whether or not a suspected object is enclosed in the inspection object from the obtained X-ray image and to detect a coordinate position of the suspected object in the inspection object;
   using the inspection device to radiate a terahertz wave or a millimeter wave onto the suspected object in the inspection object which has been determined to be thinner than the predetermined thickness and determined to have the suspected object enclosed therein on the basis of the coordinate position, and determining whether or not the suspected object is a predetermined object by detecting a scattered wave, a transmitted wave, or a reflected wave of the terahertz wave or millimeter wave; and
   sorting each inspection object into one of an inspection object which is determined to be thicker than the predetermined thickness, an inspection object which is determined to be thinner than the predetermined thickness and to have a predetermined object enclosed therein, and an inspection object which is determined to be thinner than the predetermined thickness and not to have the predetermined object enclosed therein.

2. The enclosure inspection and sorting method according to claim 1, wherein a conveyance speed of the inspection object which has been determined to have the suspected object therein is reduced prior to radiating a terahertz wave or a millimeter wave onto the inspection object.

3. The enclosure inspection method according to claim 1, further comprising, if it is determined that the suspected object is enclosed in the inspection object, relatively moving the inspection object and a radiating position of a terahertz wave or a millimeter wave to position the suspected object in the radiating position of the terahertz wave or millimeter wave.

4. The enclosure inspection and sorting method according to claim 1, wherein the inspection object in which the suspected object is enclosed is moved in a direction orthogonal to a conveyance direction so that the suspected object may pass through a radiating position where a terahertz wave or a millimeter wave is radiated onto the inspection object.

5. An enclosure inspection and sorting apparatus comprising:
   a conveyor for conveying an inspection object;
   a thickness detector for determining whether or not the thickness of the inspection object conveyed by the conveyor is thicker than a predetermined thickness;
   an X-ray inspecting device for radiating X-rays onto inspection object conveyed by the conveyor, to determine whether or not a suspected object is enclosed in the inspection object from an obtained X-ray image and to detect a coordinate position of the suspected object in the inspection object;
   an inspection device for radiating a terahertz wave or millimeter wave, onto the suspected object in the inspection object which has a thickness thinner than the predetermined thickness, from the exterior of the inspection object on the basis of the coordinate position to determine whether or not the suspected object is a predetermined object by detecting a scattered wave, a transmitted wave, or a reflected wave of the terahertz wave or millimeter wave; and
   a sorter for sorting each inspection object into one of an inspection object thicker than the predetermined thickness, an inspection object which is determined to be thinner than the predetermined thickness and not to have the predetermined object enclosed therein, and an inspection object which is determined to be thinner than the predetermined thickness and to have the predetermined object enclosed therein.

6. The enclosure inspection and sorting apparatus according to claim 5, wherein the conveyor reduces the conveyance speed of the inspection object when the inspection device radiates a terahertz wave or a millimeter wave on the inspection object which is determined to have the suspected object enclosed therein.

7. The enclosure inspection and sorting apparatus according to claim 5, and further comprising a positioner for relatively moving the conveyor and the inspection device in a direction orthogonal to a conveyance direction so that the suspected object may pass through a radiating position where the terahertz wave or millimeter wave is radiated.

8. The enclosure inspection and sorting apparatus according to claim 5, and further comprising a visual inspecting apparatus to image the inspection object for visual inspection of the inspection object.

* * * * *